(12) United States Patent
Schulte et al.

(10) Patent No.: US 9,347,051 B2
(45) Date of Patent: May 24, 2016

(54) COAGULATION FACTOR X POLYPEPTIDES WITH MODIFIED ACTIVATION PROPERTIES

(75) Inventors: Stefan Schulte, Marburg (DE); Hans-Peter Hauser, Marburg (DE); Uwe Kalina, Marburg (DE); Thomas Weimer, Gladenbach (DE)

(73) Assignee: CSL BEHRING GMBH, Marburg (DE)

( * ) Notice: Subject to any disclaimer, the term of this patent is extended or adjusted under 35 U.S.C. 154(b) by 1521 days.

(21) Appl. No.: 12/224,182

(22) PCT Filed: Feb. 19, 2007

(86) PCT No.: PCT/EP2007/001417
§ 371 (c)(1),
(2), (4) Date: Aug. 20, 2008

(87) PCT Pub. No.: WO2007/096116
PCT Pub. Date: Aug. 30, 2007

(65) Prior Publication Data
US 2009/0175828 A1    Jul. 9, 2009

Related U.S. Application Data

(60) Provisional application No. 60/780,066, filed on Mar. 8, 2006.

(30) Foreign Application Priority Data

Feb. 21, 2006    (EP) .................................... 06003475

(51) Int. Cl.
| | | |
|---|---|---|
| C07K 19/00 | (2006.01) | |
| C07K 4/12 | (2006.01) | |
| C07K 14/745 | (2006.01) | |
| C12N 9/64 | (2006.01) | |
| A61K 38/01 | (2006.01) | |
| A61K 38/36 | (2006.01) | |

(52) U.S. Cl.
CPC .............. *C12N 9/647* (2013.01); *A61K 38/012* (2013.01); *A61K 38/36* (2013.01); *C12N 9/6432* (2013.01); *C12Y 304/21006* (2013.01)

(58) Field of Classification Search
None
See application file for complete search history.

(56) References Cited

U.S. PATENT DOCUMENTS

| | | | |
|---|---|---|---|
| 4,501,731 A | 2/1985 | Tishkoff et al. | |
| 4,784,950 A | 11/1988 | Hagen et al. | |
| 6,562,598 B1* | 5/2003 | Himmelspach et al. | 435/69.6 |
| 6,573,071 B1 | 6/2003 | Himmelspach et al. | |
| 7,329,724 B2 | 2/2008 | Araki et al. | |
| 2003/0138914 A1 | 7/2003 | Himmelspach | |
| 2003/0181381 A1* | 9/2003 | Himmelspach et al. | 514/12 |
| 2005/0202527 A1* | 9/2005 | Le Bonniec et al. | 435/69.1 |
| 2009/0053185 A1 | 2/2009 | Schulte et al. | |

FOREIGN PATENT DOCUMENTS

| | | |
|---|---|---|
| EP | 1 728 798 A1 | 12/2006 |
| FR | 2 841 904 A1 | 1/2004 |
| WO | WO 98/38317 A1 | 9/1998 |
| WO | WO 98/38318 A1 | 9/1998 |
| WO | WO 98/39456 A1 | 9/1998 |
| WO | WO 01/10896 A | 2/2001 |
| WO | WO 03/006054 A1 | 1/2003 |
| WO | WO 03/035861 A2 | 5/2003 |
| WO | WO 03/035861 A3 | 5/2003 |
| WO | WO 2004/005347 A1 | 1/2004 |
| WO | WO 2006/128668 | 12/2006 |

OTHER PUBLICATIONS

Richard, Protein stability: still an unsolved problem (1997) Cell Mol. Life Sci. 53:790-80.*
Volkel et al, Engineering of human coagulation factor X variants activated by prostate-specific antigen, vol. 29, No. 1, 19-30, DOI: 10.1385/MB:29:1:19.*
Wolf, D.L., et al., "Design of Constructs for the Expression of Biologically Active Recombinant Human Factors X and XA," *Journal of Biological Chemistry*, Jul. 25, 1991, vol. 266, No. 21, pp. 13726-13730.
Bettini et al., Book review of "Handbook of Pharmaceutical Excipients," Third Edition, Arthur H. Kibbe (ed.), Pharmaceutical Press, London, 2000; in Journal of Controlled Release, vol. 71, pp. 352-353 (2001).
Camire et al., "Enhanced γ-Carboxylation of Recombinant Factor X Using a Chimeric Construct Containing the Prothrombin Propeptide," Biochemistry, vol. 39, pp. 14322-14329 (2000).
Erhardtsen, "To General Haemostatis—the Evidence-Based Route," Pathophysiology of Haemostasis and Thrombosis, vol. 32, Suppl. 1, pp. 47-52 (2002).
Himmelspach et al., "A Fully Recombinant Partial Prothrombin Complex Effectively Bypasses fVIII In Vitro and In Vivo," Thromb. Haemost., vol. 88, pp. 1003-1011 (2002).
Lee, Book review of "Pharmaceutical Formulation Development of Peptides and Proteins," Frokjaer et al., Taylor & Francis, Andover, UK, 2000; in European Journal of Pharmaceutics and Biopharmaceutics, vol. 50, p. 329 (2000).
Leytus et al., "Characterization of a cDNA Coding for Human Factor X," Proc. Natl. Acad. Sci. USA, vol. 81, pp. 3699-3702 (1984).
Ni et al., "Normalization of the Haemostatic Plugs of Dogs with Haemophilia A (Factor VIII Deficiency) Following the Infusion of a Combination of Factor Xa and Phosphatidylcholine/Phosphatidylserine Vesicles," Thrombosis and Haemostasis, vol. 67, pp. 264-271 (1992).

(Continued)

*Primary Examiner* — Maria Marvich
(74) *Attorney, Agent, or Firm* — Finnegan, Henderson, Farabow, Garrett & Dunner, LLP

(57) ABSTRACT

The present invention relates to modified cDNA sequences coding for factor X polypeptides, in particular human factor X and its derivatives which can bypass the need for either factor VIIIa/factor IXa or factor VIIa/tissue factor for activation. The invention relates further to recombinant expression vectors containing such modified cDNA sequences, host cells transformed with such recombinant expression vectors, recombinant polypeptides and derivatives which do have biological activities of the unmodified wild type protein but having altered activation properties, and processes for the manufacture of such recombinant proteins and their derivatives. The invention also covers a transfer vector for use in human gene therapy, which comprises such modified DNA sequences.

4 Claims, 4 Drawing Sheets

(56) References Cited

OTHER PUBLICATIONS

Figure 3:
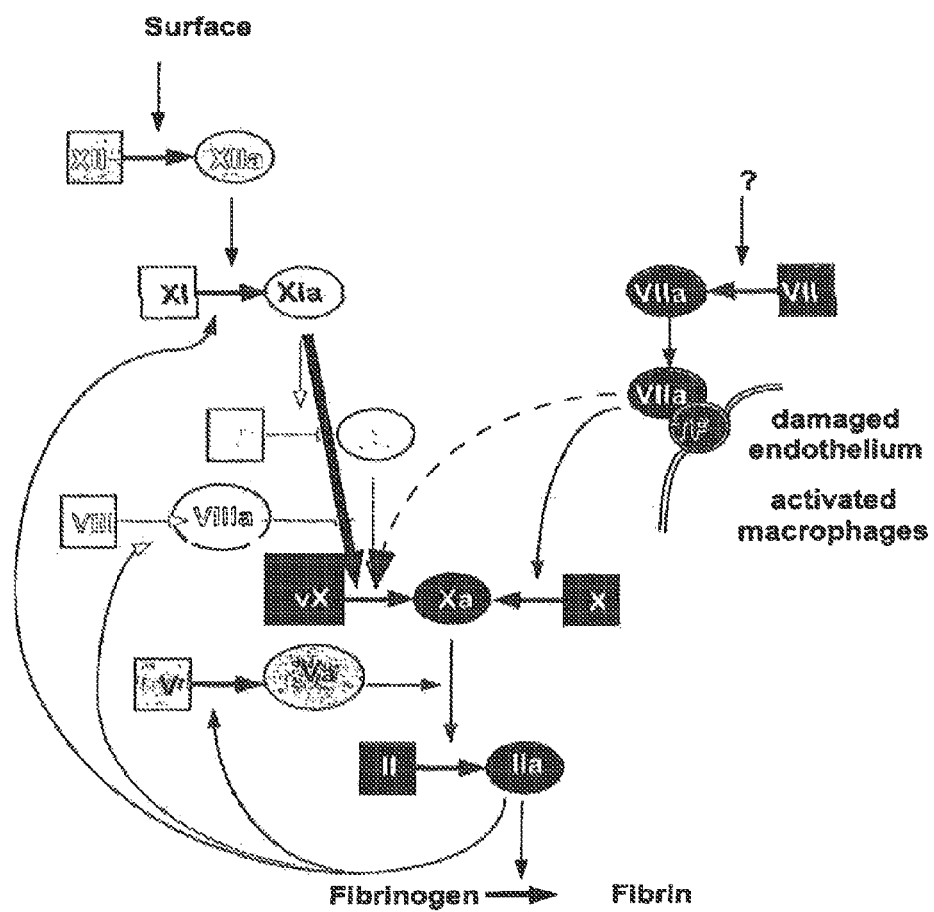

O'Reilly et al., "Antiangiogenic Activity of the Cleaved Conformation of the Serpin Antithrombin," Science, vol. 285, pp. 1926-1928 (1999).
Rudolph et al., "Expression, Purification, and Characterization of Recombinant Human Factor X," Protein Expression and Purification, vol. 10, pp. 373-378 (1997).
Rudolph et al., "The Role of the Factor X Activation Peptide: A Deletion Mutagenesis Approach," Thromb. Haemost., vol. 88, pp. 756-762 (2002).
Thiec et al., "Role of the Gla and First Epidermal Growth Factor-like Domains of Factor X in the Prothrombinase and Tissue Factor-Factor VIIa Complexes," The Journal of Biological Chemistry, vol. 278, pp. 10393-10399 (2003).
Völkel et al., "Engineering of Human Coagulation Factor X Variants Activated by Prostate-Specific Antigen," Molecular Biotechnology, vol. 29, pp. 19-30 (2005).
Wolf et al., "Procoagulant Activity of Reversibly Acylated Human Factor Xa," Blood, vol. 86, pp. 4153-4157 (1995).
"Hemostasis and Thrombosis, Basic Principles and Clinical Practice," Fourth Edition, Colman et al., 2001, pp. 34-35 and 176.
Chang, Y.J., et al., "Identification of functionally important residues of the epidermal growth factor-2 domain of factor IX by alanine-scanning mutagenesis. Residues Asn(89)-Gly(93) are critical for binding factor VIIIa," J. Biol. Chem. 277(28): 25393-9 (2002). (abstract only).
Hertzberg, M., "Biochemistry of Factor X," Blood Reviews 8: 56-62 (1994).
Peyvandi, F., et al., "Gene mutations and three-dimensional structural analysis in 13 families with severe factor X deficiency," Br. J. Haematol. 117(3): 685-92 (2002). (abstract only).
Venkateswarlu, D., et al., "Structure and Dynamics of Zymogen Human Blood Coagulation Factor X," *Biophysical Journal* 82: 1190-1206 (2002).
Bianchini et al., "Mapping of the Catalytic Groove Preferences of Factor Xa Reveals an Inadequate Selectivity for Its Macromolecule Substrates," *J. Biol. Chem.*, 277: 20527-34 (2002).
Guo et al., "Protein Tolerance to Random Amino Acid Change," PNAS, 101(25): 9205-9210 (2004).
Lesk et al., "Prediction of Protein Function from Protein Sequence and Structure," Q. Rev. Biophys., 36(3): 307-340 (2003).
Torchilin et al., "Peptide and Protein Drug Delivery to and into Tumors: Challenges and Solutions," DDT, 8(6): 259-266 (2003).
Wang W., "Instability, Stabilization and Formulation of Liquid Protein Pharmaceuticals," Int. J. Pharm, 185, 129-188 (1999).
European Search Report for Application No. 05011773.8-2405, mailed Oct. 7, 2005.
Chang et al., "Selective Cleavage Antibody Light Chains at the Joints of Variable with Joining Regions and Joining with Constant Regions," Eur. J. Biochem., 151(2):225-230 (1985).
Mizuno et al., "Crystal Structure of an Anticoagulant Protein in Complex with the Gla Domain of Factor X," PNAS, 98(13): 7230-7234 (2001).
Jenny et al., "A Critical Review of the Methods for Cleavage of Fusion Proteins with Thrombin and Factor Xa," Protein Expression and Purification, 31:1-11 (2003).
Rezaie A.R., "Identification of Basic Residues in the Heparin-binding Exosite of Factor Xa Critical for Heparin and Factor Va Binding," J. Biol. Chem., 275(5): 3320-3327 (2000).
Claeson G., "Synthetic Peptides and Peptidomimetics as Substrates and Inhibitors of Thrombin and Other Proteases in the Blood Coagulation System," Blood Coagulation and Fibrinolysis, 5(3): 411-436 (1994).
Poreba et al., "Current Strategies for Probing Substrate Specificity of Proteases," Curr. Med. Chem., 17(33): 3968-3995 (2010).

* cited by examiner

FIG. 1

|  | Light Chain | Activation Peptide | Heavy Chain |
|---|---|---|---|
| 532 | ..PYPCGKQTLERRK | SVAQATSSSGEAPDSITWKPYDAADLDPTENPFDLLDFNQTQPERGDNNLT | IVGGQECKD.. |
| 641 | ..PYPCGKQTLERRK | SVAQATSSSGEAPDSITWKPYDAADLDPTENPFDLLDFNQTQPERGDNNDD | IVGGQECKD.. |
| 535 | ..PYPCGKQTLERRK | SVAQATSSSGEAPDSITWKPYDAADLDPTENPFDLLDFNQTQPTQSFNDFT | IVGGQECKD.. |
| 915 | ..PYPCGKQTLERRK | TQSFNDFT | IVGGQECKD.. |
| 1066 | ..PYPCGKQTLERRK | TQSFNDFT | VVGGQECKD.. |

FIG. 2A

Wild type Factor X cDNA and amino acid sequence

```
atg ggg cgc cca ctg cac ctc gtc ctg ctc agt gcc tcc ctg gct ggc      48
Met Gly Arg Pro Leu His Leu Val Leu Leu Ser Ala Ser Leu Ala Gly
1               5                   10                  15 ctc ctg ctg ctc ggg gaa agt ctg ttc atc cgc agg gag cag gcc aac      96
Leu Leu Leu Leu Gly Glu Ser Leu Phe Ile Arg Arg Glu Gln Ala Asn
                20                  25                  30 aac atc ctg gcg agg gtc acg agg gcc aat tcc ttt ctt gaa gag atg     144
Asn Ile Leu Ala Arg Val Thr Arg Ala Asn Ser Phe Leu Glu Glu Met
            35                  40                  45 aag aaa gga cac ctc gaa aga gag tgc atg gaa gag acc tgc tca tac     192
Lys Lys Gly His Leu Glu Arg Glu Cys Met Glu Glu Thr Cys Ser Tyr
        50                  55                  60 gaa gag gcc cgc gag gtc ttt gag gac agc gac aag acg aat gaa ttc     240
Glu Glu Ala Arg Glu Val Phe Glu Asp Ser Asp Lys Thr Asn Glu Phe
65                  70                  75                  80 tgg aat aaa tac aaa gat ggc gac cag tgt gag acc agt cct tgc cag     288
Trp Asn Lys Tyr Lys Asp Gly Asp Gln Cys Glu Thr Ser Pro Cys Gln
                85                  90                  95 aac cag ggc aaa tgt aaa gac ggc ctc ggg gaa tac acc tgc acc tgt     336
Asn Gln Gly Lys Cys Lys Asp Gly Leu Gly Glu Tyr Thr Cys Thr Cys
                100                 105                 110 tta gaa gga ttc gaa ggc aaa aac tgt gaa tta ttc aca cgg aag ctc     384
Leu Glu Gly Phe Glu Gly Lys Asn Cys Glu Leu Phe Thr Arg Lys Leu
            115                 120                 125 tgc agc ctg gac aac ggg gac tgt gac cag ttc tgc cac gag gaa cag     432
Cys Ser Leu Asp Asn Gly Asp Cys Asp Gln Phe Cys His Glu Glu Gln
        130                 135                 140 aac tct gtg gtg tgc tcc tgc gcc cgc ggg tac acc ctg gct gac aac     480
Asn Ser Val Val Cys Ser Cys Ala Arg Gly Tyr Thr Leu Ala Asp Asn
145                 150                 155                 160 ggc aag gcc tgc att ccc aca ggg ccc tac ccc tgt ggg aaa cag acc     528
Gly Lys Ala Cys Ile Pro Thr Gly Pro Tyr Pro Cys Gly Lys Gln Thr
                165                 170                 175 ctg gaa cgc agg aag agg tca gtg gcc cag gcc acc agc agc agc ggg     576
Leu Glu Arg Arg Lys Arg Ser Val Ala Gln Ala Thr Ser Ser Ser Gly
                180                 185                 190 gag gcc cct gac agc atc aca tgg aag cca tat gat gca gcc gac ctg     624
Glu Ala Pro Asp Ser Ile Thr Trp Lys Pro Tyr Asp Ala Ala Asp Leu
            195                 200                 205 gac ccc acc gag aac ccc ttc gac ctg ctt gac ttc aac cag acg cag     672
Asp Pro Thr Glu Asn Pro Phe Asp Leu Leu Asp Phe Asn Gln Thr Gln
        210                 215                 220 cct gag agg ggc gac aac aac ctc acc agg atc gtg gga ggc cag gaa     720
Pro Glu Arg Gly Asp Asn Asn Leu Thr Arg Ile Val Gly Gly Gln Glu
225                 230                 235                 240
```

FIG. 2B

```
tgc aag gac ggg gag tgt ccc tgg cag gcc ctg ctc atc aat gag gaa      768
Cys Lys Asp Gly Glu Cys Pro Trp Gln Ala Leu Leu Ile Asn Glu Glu
            245                 250                 255 aac gag ggt ttc tgt ggt gga acc att ctg agc gag ttc tac atc cta      816
Asn Glu Gly Phe Cys Gly Gly Thr Ile Leu Ser Glu Phe Tyr Ile Leu
            260                 265                 270 acg gca gcc cac tgt ctc tac caa gcc aag aga ttc aag gtg agg gta      864
Thr Ala Ala His Cys Leu Tyr Gln Ala Lys Arg Phe Lys Val Arg Val
            275                 280                 285 ggg gac cgg aac acg gag cag gag gag ggc ggt gag gcg gtg cac gag      912
Gly Asp Arg Asn Thr Glu Gln Glu Glu Gly Gly Glu Ala Val His Glu
    290                 295                 300 gtg gag gtg gtc atc aag cac aac cgg ttc aca aag gag acc tat gac      960
Val Glu Val Val Ile Lys His Asn Arg Phe Thr Lys Glu Thr Tyr Asp
305                 310                 315                 320 ttc gac atc gcc gtg ctc cgg ctc aag acc ccc atc acc ttc cgc atg     1008
Phe Asp Ile Ala Val Leu Arg Leu Lys Thr Pro Ile Thr Phe Arg Met
                325                 330                 335 aac gtg gcg cct gcc tgc ctc ccc gag cgt gac tgg gcc gag tcc acg     1056
Asn Val Ala Pro Ala Cys Leu Pro Glu Arg Asp Trp Ala Glu Ser Thr
                340                 345                 350 ctg atg acg cag aag acg ggg att gtg agc ggc ttc ggg cgc acc cac     1104
Leu Met Thr Gln Lys Thr Gly Ile Val Ser Gly Phe Gly Arg Thr His
            355                 360                 365 gag aag ggc cgg cag tcc acc agg ctc aag atg ctg gag gtg ccc tac     1152
Glu Lys Gly Arg Gln Ser Thr Arg Leu Lys Met Leu Glu Val Pro Tyr
        370                 375                 380 gtg gac cgc aac agc tgc aag ctg tcc agc agc ttc atc atc acc cag     1200
Val Asp Arg Asn Ser Cys Lys Leu Ser Ser Ser Phe Ile Ile Thr Gln
385                 390                 395                 400 aac atg ttc tgt gcc ggc tac gac acc aag cag gag gat gcc tgc cag     1248
Asn Met Phe Cys Ala Gly Tyr Asp Thr Lys Gln Glu Asp Ala Cys Gln
                405                 410                 415 ggg gac agc ggg ggc ccg cac gtc acc cgc ttc aag gac acc tac ttc     1296
Gly Asp Ser Gly Gly Pro His Val Thr Arg Phe Lys Asp Thr Tyr Phe
                420                 425                 430 gtg aca ggc atc gtc agc tgg gga gag ggc tgt gcc cgt aag ggg aag     1344
Val Thr Gly Ile Val Ser Trp Gly Glu Gly Cys Ala Arg Lys Gly Lys
            435                 440                 445 tac ggg atc tac acc aag gtc acc gcc ttc ctc aag tgg atc gac agg     1392
Tyr Gly Ile Tyr Thr Lys Val Thr Ala Phe Leu Lys Trp Ile Asp Arg
    450                 455                 460 tcc atg aaa acc agg ggc ttg ccc aag gcc aag agc cat gcc ccg gag     1440
Ser Met Lys Thr Arg Gly Leu Pro Lys Ala Lys Ser His Ala Pro Glu
465                 470                 475                 480 gtc ata acg tcc tct cca tta aag tga                                  1467
Val Ile Thr Ser Ser Pro Leu Lys  *
                485
```

COAGULATION FACTOR X POLYPEPTIDES WITH MODIFIED ACTIVATION PROPERTIES

CROSS REFERENCE TO RELATED APPLICATIONS

This application is a national stage filing under 35 U.S.C. §371 of International Application No. PCT/EP2007/001417, filed on Feb. 19, 2007, and claims the benefit of priority of European Application No. 06003475.8, filed on Feb. 21, 2006, and U.S. Provisional Application No. 60/780,066, filed Mar. 8, 2006. All of these applications are incorporated herein by reference in their entirety.

FIELD OF THE INVENTION

The present invention relates to modified cDNA sequences coding for factor X (FX) polypeptides, in particular human factor X and its derivatives which can bypass the need for either factor VIIIa/factor IXa or factor VIIa/tissue factor for activation. The invention relates further to recombinant expression vectors containing such modified cDNA sequences, host cells transformed with such recombinant expression vectors, recombinant polypeptides and derivatives which do have biological activities of the unmodified wild type protein but having altered activation properties, and processes for the manufacture of such recombinant proteins and their derivatives. The invention also covers a transfer vector for use in human gene therapy, which comprises such modified DNA sequences.

BACKGROUND OF THE INVENTION

Vitamin K dependent proteins are used to treat certain types of hemophilia. Classic hemophilia or hemophilia A is an inherited bleeding disorder. It results from a chromosome X-linked deficiency of blood coagulation factor VIII (FVIII), and affects almost exclusively males with an incidence between one and two individuals per 10,000. The X-chromosome defect is transmitted by female carriers who are not themselves hemophiliacs. The clinical manifestation of hemophilia A is an increased bleeding tendency. Before treatment with factor VIII concentrates was introduced the mean life span for a person with severe hemophilia was less than 20 years. The use of concentrates of factor VIII from plasma and later on that of recombinant forms of factor VIII has considerably improved the situation for the hemophilia patients increasing the mean life span extensively, giving most of them the possibility to live a more or less normal life. Hemophilia B being 5 times less prevalent than hemophilia A is caused by non-functional or missing factor IX (FIX) and is treated with factor IX concentrates from plasma or a recombinant form of factor IX. In both hemophilia A and in hemophilia B the most serious medical problem in treating the disease is the generation of alloantibodies against the replacement factors. Up to 30% of all hemophilia A patients develop antibodies to factor VIII. Antibodies to FIX occur to a lesser extent but with more severe consequences, as they are less susceptible to immune tolerance induction therapy.

The current model of coagulation states that the physiological trigger of coagulation is the formation of a complex between tissue factor (TF) and factor VIIa (FVIIa) on the surface of TF expressing cells, which are normally located outside the vasculature and only get accessible once an injury occurs. The complex of factor VIIa/TF activates factor IX and factor X ultimately generating some thrombin. In a positive feedback loop thrombin activates factor VIII and factor IX which then also activate factor X, the so-called "intrinsic" arm of the blood coagulation cascade, thus amplifying the generation of factor Xa (FXa), which is necessary for the generation of the full thrombin burst to achieve complete hemostasis. It was shown that by administering supraphysiological concentrations of FVIIa hemostasis is achieved bypassing the need for factor VIIIa (FVIIIa) and factor IXa (FIXa). The cloning of the cDNA for factor VII (FVII) (U.S. Pat. No. 4,784,950) made it possible to develop a recombinant replacement of that plasma derived coagulation factor. This factor VIIa was successfully administered for the first time in 1988 to a patient with a high titer of inhibitory antibodies to FVIII. Ever since the number of indications of factor VIIa has grown steadily showing a potential for factor VIIa to become an universal hemostatic agent (Erhardtsen, 2002). Unfortunately factor VIIa has only a plasma half-life of slightly above 2 hours and must thus be readministered frequently making such therapy invasive and very expensive.

There is thus an ongoing need for improved coagulation factors, especially such that are haemostatic bypassing agents. Haemostatic bypassing agents are substances, which allow coagulation to occur when administered to patients in whom certain coagulation factors are missing, non-functional or blocked by inhibitory antibodies. The activity of such compounds to bypass blocks in the coagulation cascade (haemostatic bypassing activity) can be measured by coagulation assays known in the art. Essentially haemostatic bypassing agents have the ability to activate substrates of a missing, non-functional or blocked coagulation factor or other substrates in the coagulation cascade "downstream" of the missing, non-functional or blocked coagulation factor in a direct way such that the missing, non-functional or blocked coagulation factor is no longer needed for effective thrombin generation.

Also factor X has been the subject of extensive research.

The cDNA for factor X has been characterized (Leytus et al. 1984, PNAS, 82: 3699-3702). Coagulation factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids ($M_r$ 16,200) and a C-terminal heavy chain of 306 amino acids ($M_r$ 42,000) which are covalently linked via a disulfide bridge between Cys172 and Cys342. Further posttranslational processing steps include the β-hydroxylation of Asp103 as well as N- and O-type glycosylation.

Both factor VIIIa/factor IXa or factor VIIa/TF are under physiological conditions able to activate factor X on activated platelet surfaces by cleaving carboxy-terminal to Arg234, thus liberating the so called activation peptide of 52 amino acids from Ser183 to Arg234.

In an autocatalytic cleavage activated factor X (factor Xa) cleaves off a small fragment at the C-terminal end of its heavy chain carboxy-terminal to Arg464 leading to factor Xaβ. However the physiological relevance of this cleavage is not clear as both forms of factor Xa have comparable catalytic activities.

Several attempts have been made to modify factor X:

Wolf et al. 1991 (*JBC*, 266, no. 21, pp. 13726-13730) deleted the activation peptide of factor X replacing it with the dipeptide Arg-Lys which leads to the introduction of 2 novel furin cleavage consensus sites within the region of the activation peptide of factor X. Such factor X variants are already activated during intracellular processing leading thus to the secretion of activated factor X.

Wolf et al. 1995 (*Blood*, 86, pp 4153-4157) produced acylated inactive variants of factor Xa, which are slowly deacylated after injection into blood plasma thereby generating activated factor X over time.

Rudolph et al. 1997 (*Prot. Express and Puri.*, 10: 373-378) modified factor X in the region of the propeptide cleavage site and found that replacement of Thr39 by Arg improved the efficacy of propeptide processing in cell culture considerably.

Camire et al. 2000 (*Biochemistry*, 39 pp. 14322-14329) achieved a higher degree of gamma carboxylation in cell culture by replacing the prepropeptide of factor X by that of thrombin. However though the rate of gamma carboxylation was increased 10-30% of factor X remained uncarboxylated.

Rudolph et al., 2002 (*Thromb Haemost.*, 88:756-62) created factor X variants with deleted activation peptide. It could be seen that such factor X variants were auto-activated in a cofactor independent way and the paper concludes that the primary function of the activation peptide is to prevent spurious activation of FX.

Thiec et al. 2003 (*JBC*, 12, pp 10393-10399) replaced the Gla domain and the first EGF domain of factor X with the corresponding domain of FIX to investigate the ability of such chimeras to interact productively with the TF/FVIIa complex.

WO 98/38317 (Priority: 27 Feb. 1997) claims factor X analogues with a modification at the site of the natural activation cleavage site between Gly228 and Ile235 such that proteases which do not naturally activate factor X can cleave and activate such factor X analogues.

WO 98/38318 (Priority: 27 Feb. 1997) teaches factor X analogues in which amino acids Arg180 to Arg234 are deleted and amino acids from Gly173 to Arg179 are modified such that proteases, which do not naturally activate FX, can cleave the modified sequence thus activating the factor X analogues described above.

WO 01/10896 (Priority: 10 Aug. 1999) describes factor X analogues, which have substitutions of at least one of the amino acids between Glu226 and Ile235. In the example the introduction of a FIX derived activation cleavage site is shown which makes the factor X variant cleavable by factor XI (FXI).

According to preferred embodiments of the present invention the new protease processing site in the activation peptide of the modified factor X variant can be cleaved by a serine protease. More preferably, the serine protease is selected from the group consisting of factor IIa (FIIa), factor IXa, factor Xa, factor XIa (FXIa), factor XIIa (FXIIa), activated protein C, elastase or kallikrein.

WO 2004/005347 (Priority: 3 Jul. 2002) teaches variants of factor X which can be activated by thrombin by modifying the residues $P_3$—$P_2$—$P_1$—$P_1'$—$P_2'$—$P_3'$ which is in wild type factor X Leu-Thr-Arg-Ile-Val-Gly to X-Pro-Arg-Ala-Y-Z.

Volkel et al (2005), *Mol. Biotechnol.*, 29 (1):19-30 teaches the introduction of a novel protease cleavage site in the FX activation peptide such that prostrate specific antigen specifically activates said FX variant.

Though some authors suggested that activated factor X (FXa) might be used as a haemostatic bypassing agent (Ni et al., 1992 (Thromb. Haemost. 67:264-271); Himmelspach et al., 2002 (Thromb. Haemost. 88:1003-1011)) some concerns remain that such pharmaceutical preparations might be thrombogenic and could lead to disseminated intravasal coagulation (DIC).

The therapeutic use of the non-activated zymogen factor X appears to be a much safer approach. U.S. Pat. No. 4,501,731 (priority 27 Jun. 1983) suggests the use of factor X as a haemostatic bypassing agent on its own. In WO 03/006054 (Priority: 10 Jul. 2001) it has been shown in addition that factor X in pharmaceutical compositions is able in combination with FVIIa to enhance the haemostatic efficacy of FVIIa synergistically.

However, as the efficacy of activation of factor X via the intrinsic pathway of coagulation is severely compromised in inhibitor patients whereas the extrinsic pathway of coagulation (due to the restricted availability of tissue factor) seems to be limited to the initiation phase of coagulation it is of advantage to modify factor X in such a way to facilitate its activation in situations in which coagulation is needed and bypassing the need of cofactors of limited availability and/or activity. The variant factor X zymogen must be stable so that it can be produced and administered without activation but that in case coagulatory activity (e.g. thrombin generation) is needed, activation occurs at higher rates without the need of the natural activators of the intrinsic and the extrinsic pathway of coagulation.

It has been described that several authors attempted to generate factor X analogues which can be activated by proteases not naturally cleaving and activating FX. The factor X analogues either had deletions of the activation peptide or a modification of the sequence of the activation peptide preceding the cleavage site at Arg234. These factor X analogues, however, exhibit insufficient haemostatic bypassing activity.

One problem addressed in the present invention is to identify haemostatic bypassing agents. In particular, there is a need for haemostatic bypassing agents, which can be used to treat patients having a high titer of factor VIII inhibitors.

In the present invention it has been surprisingly found that biologically active factor X variants having enhanced haemostatic bypassing activity (FIG. 1) can be obtained by (i) modifying the activation peptide of factor X, said modification resulting in a protease cleavage site which is not present within the activation peptide of wild type factor X, and (ii) reducing the number of amino acids in the activation peptide and/or in the C-terminal region of the light chain.

Activation peptide in the sense of this invention means a peptide or polypeptide within factor X between Ser183 and Arg234 which comprises a protease cleavage site, wherein when said protease cleavage site is cleaved by a protease said factor X is activated to factor Xa.

One aspect of the invention are biologically active factor X variants having a modification in the activation peptide, said modification resulting in a protease processing site which is not present within the amino acid sequence from Arg179 to Arg234 of wild type factor X, wherein the number of amino acids between the residues corresponding to Arg179 and Ile235 is reduced by 1 to 52 amino acids relative to wild type factor X.

Another aspect of the invention are biologically active factor X variants having a modification in the activation peptide, wherein said modification results in a protease processing site which is not present within the amino acid sequence from Arg179 to Arg234 of wild type factor X, and wherein the modified activation peptide is shorter than the activation peptide of wild type factor X. Another aspect of the invention are biologically factor X variants having a modification in the activation peptide, wherein said modification results in a protease processing site which is not present within the amino acid sequence from Ser183 to Arg234 of wild type factor X, and wherein the modified activation peptide is shorter than the activation peptide of wild type factor X.

The invention further pertains to a biologically active factor X variant having a modification in the activation peptide, said modification resulting in a protease processing site which is not present within the amino acid sequence from Ser183 to Arg234 of wild type factor X and which is not a furin processing site, wherein the modified activation peptide is shorter than the activation peptide of wild type factor X.

The cDNA sequence encoding wild type factor X and the amino acid sequence of wild type factor X are shown in SEQ ID NO:1 and SEQ ID NO:2, respectively. The numbering of amino acids within the factor X sequence as used in this application refers to the amino acid numbering of the wild type sequence as shown in SEQ ID NO:2.

The factor X variant according to the present invention is activated upon cleavage of the newly introduced protease processing site by a protease capable of cleaving said protease processing site. Usually, the factor X variant of the present invention cannot be activated by intracellular proteases such as furin. Accordingly, the factor X variant of the present invention is usually not processed to factor Xa during its expression in host cells, contrary to the variant described by Wolf et al. 1991 (JBC, 266, no. 21, pp. 13726-13730). Usually, the factor X variant of the present invention is to be administered to a patient in non-activated form, and the activation to factor Xa occurs only after administration within the body of the patient.

The variants of the present invention have a reduced number of amino acids in their activation peptide sequence and/or in the C-terminal region of the light chain, relative to the amino acid sequence of wild type Factor X. The variant may have a reduced number of amino acids between the residues corresponding to Arg179 and Ile235, or a reduced number of amino acids between the residues corresponding to Arg180 and Ile235, or a reduced number of amino acids between the residues corresponding to Lys181 and Ile235, or a reduced number of amino acids between the residues corresponding to Arg182 and Ile235; wherein the reduction in the number of amino acids is relative to the amino acid sequence of wild type factor X.

Preferably, the variants of the present invention have a reduced number of amino acids in their activation peptide sequence, relative to the amino acid sequence of wild type factor X. For example, the variants may have a reduced number of amino acids between Arg182 and the amino acid residue corresponding to Ile235, relative to the amino acid sequence of wild type factor X.

The number of amino acids as defined above, relative to wild type factor X, is reduced by 1 to 52 amino acids, preferably by 5 to 49 amino acids, more preferably by 10 to 48 amino acids, more preferably by 20 to 47 amino acids, still more preferably by 30 to 47 amino acids, most preferably by 38 to 47 amino acids (e.g. by 39, 40, 41, 42, 43, 44, 45 or 46 amino acids).

The reduction in the number of amino acids may be due to deletion of one or more amino acids from the activation peptide and/or the light chain of the factor X sequence. There may be additional mutations including, but not limited to, substitutions and insertions relative to the amino acid sequence of wild type factor X.

The term "protease processing site" as used herein refers to an amino acid sequence that is recognized and cleavable by a protease. The chemical bond which is eventually cleaved by the protease may be located internally within the processing site or C-terminal to the processing site. By way of example, if the processing site is TQSFNDFTR (SEQ ID NO:3), the actual cleavage may occur C-terminal to the arginine in that sequence. Preferably, the new processing site is located in the C-terminal region of the modified activation peptide, e.g. in the region where the activation processing site of wild type factor X is located.

Cleavage by said protease of the protease processing site leads to activation of the factor X variant.

In another aspect of the present invention, the natural factor X activation peptide in the factor X variants is modified such that proteases, which naturally activate factor X, are no longer able to cleave and activate said factor X variant. This may be achieved by introducing mutations into the activation peptide sequence of factor X. Mutations include insertions, deletions and substitutions. Preferred are deletions and/or substitutions in the activation peptide sequence such that proteases, which naturally activate factor X, are no longer able to cleave and activate said factor X variant, such that activation occurs only via the new protease processing site. Most preferably the protease processing site present in the activation peptide of wild type factor X is replaced with a protease processing site for a protease that does not naturally cleave and activate wild type factor X.

According to preferred embodiments of the present invention the new protease processing site in the activation peptide of the modified factor X variant can be cleaved by a serine protease. More preferably, the serine protease is selected from the group consisting of factor IIa, factor IXa, factor Xa, factor XIa, factor XIIa, activated protein C, elastase or kallikrein.

In one embodiment, the modified activation peptide in the factor X variant of the present invention is represented by the following formula:

$$-R^1-P-R^2-,$$

wherein P designates an amino acid sequence cleavable by the cleaving protease, i.e. the amino acid sequence which is recognized and can be cleaved by the cleaving protease, designated also as "processing site",
$R^1$ designates a chemical bond or one or more amino acids (e.g. 1 to 48 amino acids), and
$R^2$ designates a chemical bond or one or more amino acids (e.g. 1 to 5 amino acids).

The modified activation peptide in the factor X variant according to the present invention is preferably shorter than the activation peptide of wild type factor X. Accordingly, the maximum length of $-R^1-P-R^2-$ is usually 51 amino acids. The total length of $-R^1-P-R^2-$ preferably ranges from 3 to 40 amino acids, more preferably from 4 to 40 amino acids, still more preferably from 5 to 30 amino acids, even more preferably from 6 to 20 amino acids, most preferably from 7 to 15 amino acids, e.g. 7, 8, 9, 10, 11, 12, 13, 14 or 15 amino acids.

$R^1$ may have a length of up to 48 amino acids. Preferably, however, $R^1$ is a chemical bond or consists of 1 to 20, preferably of 1 to 10 amino acids (e.g. of 1, 2 or 3 amino acids). $R^1$ may be a partial sequence of the activation peptide of wild type factor X. The amino acid sequence of the activation peptide of wild type factor X, consisting of 52 amino acids, is shown in SEQ ID NO:4. For example, $R^1$ may comprise, or consist of, an N-terminal or internal fragment within amino acids 1-45 of SEQ ID NO:4. Examples of $R^1$ include, but are not limited to, the following sequences:
amino acid 1 of SEQ ID NO:4 (i.e. amino acid No. 1=Ser);
amino acids 1 to 2 of SEQ ID NO:4 (i.e. Ser-Val);
amino acids 1 to 3 of SEQ ID NO:4 (i.e. Ser-Val-Ala);

amino acids 1 to 4 of SEQ ID NO:4; amino acid 1 to 5 of SEQ ID NO:4;
amino acids 1 to 6 of SEQ ID NO:4; amino acids 1 to 7 of SEQ ID NO:4;
amino acids 1 to 8 of SEQ ID NO:4; amino acids 1 to 9 of SEQ ID NO:4;
amino acids 1 to 10 of SEQ ID NO:4; amino acids 1 to 11 of SEQ ID NO:4;
amino acids 1 to 12 of SEQ ID NO:4; amino acids 1 to 13 of SEQ ID NO:4;
amino acids 1 to 14 of SEQ ID NO:4; amino acids 1 to 15 of SEQ ID NO:4;
amino acids 1 to 16 of SEQ ID NO:4; amino acids 1 to 17 of SEQ ID NO:4;
amino acids 1 to 18 of SEQ ID NO:4; amino acids 1 to 19 of SEQ ID NO:4;
amino acids 1 to 20 of SEQ ID NO:4; amino acids 1 to 21 of SEQ ID NO:4;
amino acids 1 to 22 of SEQ ID NO:4; amino acids 1 to 23 of SEQ ID NO:4;
amino acids 1 to 24 of SEQ ID NO:4; amino acids 1 to 25 of SEQ ID NO:4;
amino acids 1 to 26 of SEQ ID NO:4; amino acids 1 to 27 of SEQ ID NO:4;
amino acids 1 to 28 of SEQ ID NO:4; amino acids 1 to 29 of SEQ ID NO:4;
amino acids 1 to 30 of SEQ ID NO:4; amino acids 1 to 31 of SEQ ID NO:4;
amino acids 1 to 32 of SEQ ID NO:4; amino acids 1 to 33 of SEQ ID NO:4;
amino acids 1 to 34 of SEQ ID NO:4; amino acids 1 to 35 of SEQ ID NO:4;
amino acids 1 to 36 of SEQ ID NO:4; amino acids 1 to 37 of SEQ ID NO:4;
amino acids 1 to 38 of SEQ ID NO:4; amino acids 1 to 39 of SEQ ID NO:4;
amino acids 1 to 40 of SEQ ID NO:4; amino acids 1 to 41 of SEQ ID NO:4;
amino acids 1 to 42 of SEQ ID NO:4; amino acids 1 to 43 of SEQ ID NO:4;
amino acids 1 to 44 of SEQ ID NO:4; and amino acids 1 to 45 of SEQ ID NO:4.

It is further preferred that $R^2$ is a chemical bond or consists of 1 or 2 amino acids. Most preferably $R^2$ is a chemical bond.

Generally, the amino acid C-terminal to the chemical bond which is cleaved when the newly introduced protease cleavage site is cleaved is preferably isoleucine or valine. This amino acid is preferably followed by valine. Other preferred amino acids C-terminal to the chemical bond which is cleaved when the newly introduced protease cleavage site is cleaved are alanine, serine or threonine.

When $R^2$ is a chemical bond, the amino acid C-terminal to the chemical bond which is cleaved when the newly introduced protease cleavage site is cleaved is the N-terminal amino acid of the heavy chain of the factor X variant and corresponds to Ile235. This amino acid may be Ile, Val, Ala, Ser or Thr. Preferably, the amino acid corresponding to Ile235 is Ile or Val. The amino acid corresponding to Val236 is preferably Val.

In another embodiment, $R^2$ may be Ile, Val, Ala, Ser, Thr, Ile-Val, or Val-Val.

P has a length of at least 3 amino acids and preferably not more than 30 amino acids. Preferably, P has a length of from 4 to 15 amino acids, more preferably of 4 to 10 amino acids. Cleavage by the protease usually occurs C-terminal to P. P may be a partial amino acid sequence of a protein cleaved by the cleaving protease. Alternatively, P may be a non-naturally occurring or an artificial amino acid sequence which is cleavable by the cleaving protease.

Proteins that are cleaved by a suitable protease and comprise a suitable protease processing site include coagulation factors and serpins like Factor VII, Factor IX, Antithrombin III, Factor II (FII), Factor VIII, Factor XI, Factor XII (FXII), Prekallikrein, and their amino acid sequences are known to those of skill in the art (see infra). Accordingly, P may be a partial sequence or a fragment of any one of these proteins, wherein said partial sequence or fragment comprises a protease processing site. Also encompassed in the invention are variations of these processing sites as long as they are still cleavable by the cleaving protease. The variations include amino acid substitutions, deletions, insertions and combinations thereof.

Suitable amino acid sequences P which comprise amino acid sequences that can be recognized and cleaved by serine proteases are indicated in the following items (i) to (iv):

(i) An amino acid sequence that is derived from FVII and can be cleaved by e.g. Factor Xa is the amino acid sequence LEKRNASKPQGR (SEQ ID NO:5). Further examples of amino acid sequences that are derived from FVII and can be cleaved by e.g. Factor Xa are the
amino acid sequences consisting of amino acids 2 to 12 of SEQ ID NO:5;
amino acids 3 to 12 of SEQ ID NO:5;
amino acids 4 to 12 of SEQ ID NO:5;
amino acids 5 to 12 of SEQ ID NO:5;
amino acids 6 to 12 of SEQ ID NO:5;
amino acids 7 to 12 of SEQ ID NO:5; or
amino acids 8 to 12 of SEQ ID NO:5.

(ii) An amino acid sequence that is derived from FIX and can be cleaved by e.g. FXIa is the amino acid sequence AETVFPDVDYVNSTEAETILDNITQSTQSFNDFTR (SEQ ID NO:6). Further examples of amino acid sequences that are derived from FVII and can be cleaved by e.g. FXIa are the amino acid sequences consisting of
amino acids 2 to 35 of SEQ ID NO:6; amino acids 3 to 35 of SEQ ID NO:6;
amino acids 4 to 35 of SEQ ID NO:6; amino acids 5 to 35 of SEQ ID NO:6;
amino acids 6 to 35 of SEQ ID NO:6; amino acids 7 to 35 of SEQ ID NO:6;
amino acids 8 to 35 of SEQ ID NO:6; amino acids 9 to 35 of SEQ ID NO:6;
amino acids 10 to 35 of SEQ ID NO:6; amino acids 11 to 35 of SEQ ID NO:6;
amino acids 12 to 35 of SEQ ID NO:6; amino acids 13 to 35 of SEQ ID NO:6;
amino acids 14 to 35 of SEQ ID NO:6; amino acids 15 to 35 of SEQ ID NO:6;
amino acids 16 to 35 of SEQ ID NO:6; amino acids 17 to 35 of SEQ ID NO:6;
amino acids 18 to 35 of SEQ ID NO:6; amino acids 19 to 35 of SEQ ID NO:6;
amino acids 20 to 35 of SEQ ID NO:6; amino acids 21 to 35 of SEQ ID NO:6;
amino acids 22 to 35 of SEQ ID NO:6; amino acids 23 to 35 of SEQ ID NO:6;
amino acids 24 to 35 of SEQ ID NO:6; amino acids 25 to 35 of SEQ ID NO:6;
amino acids 26 to 35 of SEQ ID NO:6; amino acids 27 to 35 of SEQ ID NO:6;
amino acids 28 to 35 of SEQ ID NO:6; amino acids 29 to 35 of SEQ ID NO:6;

amino acids 30 to 35 of SEQ ID NO:6; or amino acids 31 to 35 of SEQ ID NO:6.

(iii) An amino acid sequence that is derived from Antithrombin III and can be cleaved by e.g. Factor IIa is the amino acid sequence GSEAAASTAVVIAGRS (SEQ ID NO:7). Further examples of amino acid sequences that are derived from Antithrombin III and can be cleaved by e.g. Factor IIa are fragments of SEQ ID NO:7 which are cleavable by a protease that is capable of cleaving antithrombin Ill.

(iv) Further non-limiting examples of protease cleavage sites are amino acid sequences that can be cleaved by factor IIa, factor IXa, factor Xa, factor XIIa, activated protein C, elastase or kallikrein. The amino acid sequences which are recognized and cleaved by these serine proteases are known to one of ordinary skill (e.g. as described in "Hemostasis and Thrombosis, Basic Principles and Clinical Practice", Fourth Edition, Colman et al. 2001 factor IIa: p 34-35, p 176, factor IXa: p 40-41, factor Xa: p 3435, factor XIa p 128-129, factor XIIa: p 194, aPC: p 3435, p 159, kallikrein: p 103-104 or elastase (O'Reilly et al., 1999; Antiangiogenic activity of the cleaved conformation of the serpin antithrombin: Science, 285, 1926-1928). These amino acid sequences are incorporated herein by reference.

Fragments of protease cleavage sites are also encompassed by the invention, as long as the FX variant comprising such fragmented protease cleavage site is still susceptible to cleavage and said FX variant still has biological activity.

It is preferred that the processing site P within the structure —$R^1$—P—$R^2$— consists of an amino acid sequence selected from the group consisting of SEQ ID NO:5, SEQ ID NO:6, SEQ ID NO:7, and cleavable fragments thereof as described in the above items (i), (ii), (iii) and (iv).

It was also found that one or more amino acids at the C-terminal end of the natural light chain of the factor X sequence may be deleted. Accordingly, the factor X variant of the present invention may comprise the following structure adjacent to the modified activation peptide $R^1$—P—$R^2$:

LC—$R^1$—P—$R^2$—HC1-HC2—, wherein the meaning of $R^1$, P and $R^2$ is as defined above, LC means the C-terminal amino acid of the light chain in the factor X sequence, HC1 means the N-terminal amino acid of the heavy chain in the factor X sequence and HC2 means the second amino acid in the heavy chain in the factor X sequence. HC1 corresponds to Ile235 in the wild type sequence. HC1 may be Ile, Val, Ala, Ser or Thr. Preferably, HC1 is Ile or Val. HC2 corresponds to Val236 in the wild type sequence. HC2 may be Ile, Val, Ala, Ser or Thr. Preferably, HC2 is Ile or Val; most preferably, HC2 is Val.

LC may be any one or more of the amino acid residues from Arg179 through Arg182. LC is preferably selected from the group consisting Arg182, Lys181, Arg180 and Arg179.

More specifically, the factor X variant of the present invention may comprise the following structure:

-Arg182-$R^1$—P—$R^2$—HC1-HC2-; preferably
-Lys181-Arg182-$R^1$—P—$R^2$—HC1-HC2-; more preferably -Arg180-Lys181-Arg182-$R^1$—P—$R^2$—HC1-HC2—, wherein the meaning of $R^1$, P and $R^2$, HC1 and HC2 is as defined above.

In another embodiment, also the amino acid corresponding to Arg182 has been deleted. Accordingly, the factor X variant of the present invention may comprise the following structure:

-Lys181-$R^1$—P—$R^2$—HC1-HC2-; preferably
-Arg180-Lys181-$R^1$—P—$R^2$—HC1-HC2—;

wherein the meaning of $R^1$, P and $R^2$, HC1 and HC2 is as defined above.

In yet another embodiment, also the amino acids corresponding to Lys181 and Arg182 have been deleted. Accordingly, the factor X variant of the present invention may comprise the following structure:

-Arg180-$R^1$—P—$R^2$—HC1-HC2—;

wherein the meaning of $R^1$, P and $R^2$, HC1 and HC2 is as defined above.

In yet another embodiment, also the amino acids corresponding to Arg180, Lys181 and Arg182 have been deleted. Accordingly, the factor X variant of the present invention may comprise the following structure:

-Arg179-$R^1$—P—$R^2$—HC1-HC2—;

wherein the meaning of $R^1$, P and $R^2$, HC1 and HC2 is as defined above.

In a specific aspect, LC1 may be any one of the amino acid residues from Pro171 through Arg182 (see SEQ ID NO:2) when P is a partial amino acid sequence of factor IX with at least seven consecutive amino acids derived from the factor IX amino acid sequence. According to this aspect of the invention, P consists of an amino acid sequence selected from the group consisting of
amino acids 1 to 35 of SEQ ID NO:6, amino acids 2 to 35 of SEQ ID NO:6,
amino acids 3 to 35 of SEQ ID NO:6, amino acids 4 to 35 of SEQ ID NO:6,
amino acids 5 to 35 of SEQ ID NO:6, amino acids 6 to 35 of SEQ ID NO:6,
amino acids 7 to 35 of SEQ ID NO:6, amino acids 8 to 35 of SEQ ID NO:6,
amino acids 9 to 35 of SEQ ID NO:6, amino acids 10 to 35 of SEQ ID NO:6,
amino acids 11 to 35 of SEQ ID NO:6, amino acids 12 to 35 of SEQ ID NO:6,
amino acids 13 to 35 of SEQ ID NO:6, amino acids 14 to 35 of SEQ ID NO:6,
amino acids 15 to 35 of SEQ ID NO:6, amino acids 16 to 35 of SEQ ID NO:6,
amino acids 17 to 35 of SEQ ID NO:6, amino acids 18 to 35 of SEQ ID NO:6,
amino acids 19 to 35 of SEQ ID NO:6, amino acids 20 to 35 of SEQ ID NO:6,
amino acids 21 to 35 of SEQ ID NO:6, amino acids 22 to 35 of SEQ ID NO:6,
amino acids 23 to 35 of SEQ ID NO:6, amino acids 24 to 35 of SEQ ID NO:6,
amino acids 25 to 35 of SEQ ID NO:6, amino acids 26 to 35 of SEQ ID NO:6,
amino acids 27 to 35 of SEQ ID NO:6, amino acids 28 to 35 of SEQ ID NO:6, and
amino acids 29 to 35 of SEQ ID NO:6. Preferably, P consists of SEQ ID NO:3.

In another embodiment, the invention relates to a factor X variant comprising a factor X amino acid sequence in which amino acids Ser183 to Arg234 of SEQ ID NO:2 have been replaced with —$R^1$—P—$R^2$—, wherein the meaning of $R^1$, P and $R^2$ is as defined hereinabove. The invention further relates to a factor X variant comprising a factor X amino acid sequence in which amino acids Arg182 to Arg234 of SEQ ID NO:2 have been replaced with —$R^1$—P—$R^2$—, wherein the meaning of $R^1$, P and $R^2$ is as defined hereinabove. In another embodiment, the invention relates to a factor X variant comprising a factor X amino acid sequence in which amino acids Lys181 to Arg234 of SEQ ID NO:2 have been replaced with —R¹—P—R²—, wherein the meaning of R¹, P and R² is as defined hereinabove. In yet another embodiment, the invention relates to a factor X variant comprising a factor X amino acid sequence in which amino acids Arg180 to Arg234 of SEQ ID NO:2 have been replaced with —R¹—P—R²—, wherein the meaning of R¹, P and R² is as defined hereinabove.

In a preferred aspect, the factor X variant of the invention comprises a factor X amino acid sequence in which amino acids Ser183 to Arg234 of SEQ ID NO:2 have been replaced with any one of the amino acid sequences SEQ ID NO:5 through 7 or with a fragment thereof as described hereinabove in any one of items (i), (ii) and (iii). Most preferred is a factor X variant comprising a factor X amino acid sequence in which amino acids Ser183 to Arg234 of SEQ ID NO:2 have been replaced with the amino acid sequence as shown in SEQ ID NO:3. The complete amino acid sequences of the most preferred factor X variants are shown in SEQ ID NO:8 and SEQ ID NO:9.

Also encompassed by the present invention are embodiments where a new protease processing site as defined hereinabove has been introduced into the heavy chain of the factor X molecule. The protease processing site introduced into the heavy chain may be a further processing site in addition the protease processing site present in the modified activation peptide, or it may be present instead of the protease processing site in the modified activation peptide. Insertions into the heavy chain are preferably made C-terminal to Ile235 or a corresponding residue (e.g. Val). Insertions into the heavy chain of factor X are described in detail in European Patent application No. 05011773.8 filed on Jun. 1, 2005, the disclosure of which is incorporated herein by reference. The embodiments described therein can be combined with the embodiments described in this application.

For example, the invention encompasses factor X variants characterized by the formula

-LC—R¹—HC1-R¹—P—R²—HC2 wherein the meaning of LC, R¹, P, R², HC1 and HC2 is as defined above. In that case, R² is preferably one of Ile, Val, Ala, Ser and Thr, most preferably R² is Ile or Val.

Another example of such embodiment is a variant of the formula

-LC—R¹—HC1-HC2-R¹—P—R²—HC3- wherein the meaning of LC, R¹, P, R², HC1 and HC2 is as defined above and HC3 means the third amino acid of the heavy chain of factor X. In that embodiment, R² is preferably Ile-Val, or Val-Val.

The factor X variant of this invention may have further modifications at other positions within the factor X sequence. Accordingly, the modification and partial deletion in the activation peptide of factor X may be one of several modifications to the amino acid sequence as compared to the wild type sequence as shown in SEQ ID NO:2. It is preferred that the threonine at position 39 is replaced with arginine.

In one specific embodiment, the factor X variant of the invention has no modification in the factor X amino acid sequence between Gly173 and Arg179. In another embodiment, the factor X variant of the invention has a modification in the factor X amino acid sequence between Gly173 and Arg179, but this modification in the factor X amino acid sequence between Gly173 and Arg179 does not result in a processing site for a protease that does not naturally cleave between Gly173 and Arg179 of SEQ ID NO:2. The modification in the factor X amino acid sequence between Gly173 and Arg179 may be a deletion, substitution and/or insertion of one or more (e.g. 1, 2 or 3) amino acids.

In other specific embodiments, the activation peptide (i.e. amino acids Ser183 to Arg234) of the wild type factor X sequence is not replaced with the sequence RKR; or the structure —R¹—P—R²— as defined above is not RKR; or the factor X variant does not have the sequence -Arg182-Arg-Lys-Arg-[Ile235]- (SEQ ID NO:25).

In another embodiment, the protease processing site which is not present within the amino acid sequence from Ser183 to Arg234 of wild type factor X is not RKRRK (SEQ ID NO:26).

The factor X variants of the invention have biological activity. The term "biological activity" as used herein refers to factor X activity. A protein having factor X activity means, that the protein in its zymogen form can be activated through cleavage by a protease and has in its activated form factor Xa activity. Factor X activity can be determined in a coagulation assay in vitro. For example, factor X activity can be determined in a prothrombin time (PT) assay measuring the activity of the extrinsic coagulation pathway, as described in Example 4. Factor X activity expressed as clotting activity in a sample is given as mU/ml or U/ml.

The factor X activity so determined may be referred to the amount of factor X antigen present in the sample, thus yielding the "specific activity" of the variant, expressed exemplary in U/mg or mU/μg protein. The specific activity of the variants of the invention is preferably at least 50%, more preferably at least 75% of the factor X activity of a recombinant factor X molecule having the wild type sequence as shown in SEQ ID NO:2.

The factor X variants of the invention further have haemostatic bypassing activity. This activity can be determined as described in Example 4 by measuring the clotting activity (aPPT) using FVIII- or FIX-depleted plasma. The clotting activity in such assays is preferably more than 70 fold, more preferably more than 100 fold, most preferably more than 500 fold increased over that of recombinant factor X having the wild type sequence. The clotting activity using FVIII-depleted plasma is preferably more than 200 fold, more preferably more than 300 fold, more preferably more than 500 fold, most preferably more than 1000 fold or even more than 1500 fold increased over that of recombinant factor X having the wild type sequence. The clotting activity using FIX-depleted plasma is preferably more than 100 fold, more preferably 200 fold, most preferably more than 500 fold or more than 1000 fold increased over that of recombinant factor X having the wild type sequence.

The factor X variant has an improved bypassing activity in the presence of factor VIII inhibitors. This activity can be determined as described in example 4 infra. The clotting time in plasma containing FVIII inhibitors (e.g. as determined according to example 4) of the factor X variant of this invention is reduced by at least 25%, preferably by at least 50%, more preferably by at least 75% relative to the clotting time of recombinant factor X having the wild type sequence, when adjusted to the same factor X activity.

Preferred factor X variants according to the invention are factor X variants which have enhanced haemostatic bypassing activity compared to the factor X variants described in the prior art. For example, the factor X variants according to the invention usually have significantly enhanced haemostatic bypassing activity compared to a comparative factor X variant containing the sequence Glu226-Gln227-Ser228-Phe229-Asn230-Asp231-Phe232-Thr233-Arg234 (or EQS-FNDFTR in one-letter code) (SEQ ID NO:10), relative to the amino acid numbering of SEQ ID NO:2 (the length of the activation peptide of that comparative variant is 52 amino acids, i.e. there is no partial deletion in the length of the activation peptide). The haemostatic bypassing activity in the FVIII- or FIX-depleted plasma is increased by a factor of at least 1.5, preferably of at least 2, more preferably of at least 5, most preferably of at least 10, as compared to that comparative variant. The clotting time in plasma containing FVIII inhibitors (e.g. as determined according to example 4) of the factor X variant of this invention is reduced by at least 25%, preferably by at least 50% relative to the clotting time of that comparative variant, when adjusted to the same factor X activity.

In another embodiment, the factor X variants according to the invention have significantly enhanced haemostatic bypassing activity compared to a comparative factor X variant comprising a factor X amino acid sequence in which the amino acids 226 to 234 of SEQ ID NO:2 have been replaced with the amino acid sequence as shown in SEQ ID NO:3, wherein the length of the activation peptide in said comparative factor X variant is 52 amino acids. This comparative variant corresponds to the construct "535" described in the Examples. The haemostatic bypassing activity in the FVIII- or FIX-depleted plasma is increased by a factor of at least 1.5, preferably of at least 2, more preferably of at least 5, most preferably of at least 10, as compared to that comparative variant. The clotting time in plasma containing FVIII inhibitors (e.g. as determined according to example 4) of the factor X variant of this invention is reduced by at least 25%, preferably by at least 50% relative to the clotting time of that comparative variant, when adjusted to the same factor X activity.

Another aspect of the invention is a method for producing a haemostatic bypassing agent, comprising modifying the activation peptide of a factor X sequence such that the modified activation peptide comprises a protease processing site which is not present within the amino acid sequence from Arg179 to Arg234 of wild type factor X, and reducing the number of amino acids between the residues corresponding to Arg179 and Ile235 by 1 to 52 amino acids relative to wild type factor X.

Another aspect of the invention is a method for producing a haemostatic bypassing agent, comprising modifying the activation peptide of a factor X sequence such that the modified activation peptide comprises a protease processing site which is not present within the amino acid sequence from Arg179 to Arg234 of wild type factor X, and partially deleting the activation peptide such that the modified activation peptide is shorter than the activation peptide of wild type factor X.

Preferably, the new cleavage site is in the C-terminal region of the modified activation peptide. The preferred embodiments of the method of the invention correspond to the preferred embodiments of the factor X variant described herein.

The invention further relates to a polynucleotide encoding a modified human factor X as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extra-chromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing a variant of human factor X, which is part of this invention. The method comprises:
a) culturing host cells of the invention under conditions such that the factor X variant is expressed; and
b) optionally recovering the variant of human factor X from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

"Factor X" as used in this application means a product consisting of the nonactivated form (factor X). "Factor X" within the above definition includes proteins that have the amino acid sequence of native human factor X. It also includes proteins with a slightly modified amino acid sequence, for instance, a modified N-terminal end including N-terminal amino acid deletions or additions so long as those proteins substantially retain the activity of factor Xa. "Factor X" within the above definition also includes natural allelic variations that may exist and occur from one individual to another. "Factor X" within the above definition further includes variants of factor X. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in the following table.

TABLE 1

| (1) | Alanine | Glycine |
|---|---|---|
| (2) | Aspartic acid | Glutamic acid |
| (3a) | Asparagine | Glutamine |

TABLE 1-continued

| | | | | |
|---|---|---|---|---|
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

The term "recombinant" means, for example, that the variant has been produced in a host organism by genetic engineering techniques. The factor X variant of this invention is usually a recombinant factor X variant.

Expression of the Proposed Variants:

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the factor X variant. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins.

The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify the modified biologically active factor X variant of the present invention to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified biologically active factor X variant of the invention is substantially free of other polypeptides.

The recombinant proteins described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known an can be used to administer the composition by any convenient route. Preferentially the compositions of the invention are administered systemically. For systemic use, the factor X variants of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential route of administration is intravenous administration. The formulations can be administered continuously by infusion or by bolus injection. Some formulations encompass slow release systems.

The modified biologically active factor X variants of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical.

Another aspect of the invention is the use of a modified homologue of human factor X as described herein, of a polynucleotide of the invention, of a plasmid or vector of the invention, or of a host cell of the invention for the manufacture of a medicament for the treatment or prevention of a blood coagulation disorder. Blood coagulation disorders include but are not limited to hemophilia A, hemophilia B, or FVII/FVIIa deficiency. Preferably these diseases are caused or congenital forms are aggravated by autoimmune antibodies against the respective coagulation factors. In a specific embodiment, the patients to be treated have inhibitor antibodies against factor VIII. Preferably, the treatment comprises human gene therapy.

The invention also concerns a method of treating an individual suffering from a blood coagulation disorder such as hemophilia A, hemophilia B or FVII/FVIIa deficiency, preferably these diseases are caused by or congenital forms are aggravated by autoimmune antibodies against the respective coagulation factors. The method comprises administering to said individual an efficient amount of the modified homologue of human factor X as described herein. In another embodiment, the method comprises administering to the individual an efficient amount of the polynucleotide of the invention or of a plasmid or vector of the invention. Alternatively, the method may comprise administering to the individual an efficient amount of the host cells of the invention described herein.

DESCRIPTION OF THE TABLES AND DRAWINGS

FIG. 1:
Outline of FX wild type and of FX variants with newly introduced protease cleavage sites. Numbers refer to amino acid numbering of SEQ ID NO 2, the activation peptide being defined as the amino acid sequence from Ser183 to Arg234. Foreign activation sequences derived from factor IX are outlined in bold letters. Underlined amino acids denote point mutations, which render the respective factor X molecule non-activatable by the tenase complex and factor VIIa/tissue factor, respectively. The construct "532" corresponds to the factor X wild type sequence (the amino acid sequence from Pro169 to Asp243 of SEQ ID NO:2 is shown). The amino acid sequences shown for constructs "641," "535," "915", and "1066" correspond to SEQ ID NOs: 27, 28, 29, and 30, respectively.

FIG. 2A:
The first portion of nucleotide (SEQ ID NO:1) and amino acid (SEQ ID NO:2) sequences of wild type factor X.

FIG. 2B:
The second portion of nucleotide and amino acid sequences of wild type factor X.

FIG. 3:
Schematic view of the coagulation cascade showing how a factor X variant bearing a protease processing site from factor IX can be directly activated by factor XI bypassing the need for coagulation factors IX and VIII

EXAMPLES

Example 1

Construction of Expression Plasmids

Factor X coding sequence was amplified by PCR from a human liver cDNA library (Ambion) using primers We1292 and We1293 (SEQ ID NO 11 and 12). In a second round of PCR using primers We1354 and We1355 (SEQ ID NO 13 and 14) a cleavage site for restriction endonuclease NheI was introduced to the 5'-end and a cleavage site for restriction endonuclease NotI was introduced to the 3'-end of the fragment. The PCR fragment was then inserted into the NheI/NotI sites of pIRESpuro3 (BD Biosciences). The resulting plasmid was designated pFX-445.

To improve processing of the propeptide the cleavage site was improved by replacing amino acid threonine at position 39 (SEQ ID NO 2) by arginine (Rudolph et al., 1997 (Protein Expression and Purification 10:373-378)). For that, pFX445 was subjected to site-directed mutagenesis using oligonucleotides We1482 and We1483 (SEQ ID NO 15 and 16) according to standard methods (QuickChange XL Site Directed Mutagenesis Kit, Stratagene). The resulting plasmid was designated pFX-532.

All mutations described below were performed with a commercially available mutagenesis kit (QuickChange XL Site Directed Mutagenesis Kit, Stratagene).

Based on pFX-532, constructs with factor XIa cleavage sites were generated. Replacement mutagenesis using oligonucleotides We1444 and We1445 (SEQ ID NO 17 and 18) resulted in plasmid pFX-535 with a replacement of 8 amino acids of the factor X activation region (amino acids 225-233 of SEQ ID NO 2) by 8 amino acids from the activation region of FIX.

Site directed mutagenesis using oligonucleotides We1567 and We1568 (SEQ ID NO 19 and 20) on pFX-532 was used to generate plasmid pFX-641. It contained two mutations within the factor X activation peptide, Leu232Asp and Thr233Asp, thereby generating a factor X molecule, which could not be activated.

Deletion mutagenesis using oligonucleotides We1976 and We1977 (SEQ ID NO 21 and 22) resulted in plasmid pFX-915 with deletion of the FX activation peptide sequence but maintaining the inserted FIX activation sequence (see FIG. 3).

Site directed mutagenesis on pFX-915 using oligonucleotides We2357 and We2358 (SEQ ID NO 23 and 24) resulted in plasmid pFX-1066, wherein Ile235 was replaced by Val and thereby the aminoterminal amino acid of the heavy chain of FX was changed into the corresponding amino acid of FIX.

Example 2

Transfection and Expression of Modified Factor X Molecules

Plasmids were grown up in *E. coli* TOP10 (Invitrogen) and purified using standard protocols (Qiagen). HEK 293 cells were transfected using the Lipofectamine 2000 reagent (Invitrogen) and grown up in serum-free medium (Invitrogen 293 Express) in the presence of 50 ng/ml Vitamin K and 4 μg/ml Puromycin. About four weeks post transfection supernatants were harvested for biochemical characterization.

Example 3

Characterization of Recombinant Factor X Variants

The expression of the factor X variants was controlled by quantitative ELISA using monoclonal antibodies against factor X. Integrity of the recombinant proteins was analysed subsequently by SDS-PAGE and Western blotting. Samples were analysed under reduced and non-reduced conditions. Plasmatic factor X served as a native molecular weight control. Factor Xa was used to detect and compare any activated recombinant factor X variants in case of auto-activation. As visualized in Western blots, all recombinant factor X variants were expressed with the correct molecular weight of about 58 kDa, and migrated at a comparable position to plasmatic factor X. When reduced, the recombinant factor X variants disintegrated into a heavy chain (HC) of approximately 40 kDa and a light chain (LC) of approximately 20 kDa. The 58 kDa band represented unprocessed one-chain (OC) factor X. There was neither factor Xa nor any aggregates of factor X detected in the Western blots. Factor X variants of the invention were visualized in Western blots as unprocessed one-chain molecules with molecular weights of approximately 49 kDa. This holds true for the non-reduced as well as for the reduced forms.

Example 4

Investigation of In Vitro Activities of the Recombinant Factor X Variants in Human Factor X-, Factor VIII- and Factor IX Deficient Plasmas, as Well as in Human Factor VIII Inhibitor Plasma Factor X activity was determined in prothrombin time (PT) assay measuring the activity of the extrinsic coagulation pathway. 100 μl of factor X deficient plasma was mixed with 100 μl of factor X variant cell culture supernatant or purified protein. After incubation for 60 seconds at 37° C. 200 μl of Thromborel (Dade Behring), containing human plasma derived thromboplastin, $CaCl_2$ and phospholipids, was added to the mixture and clotting time in seconds determined by using a Schnittger & Gross coagulation timer. For determination of factor X activity, the assay was calibrated using a plasmatic factor X standard. Cell culture supernatants of mutated factor X pFX641 can serve as negative control for this assay. This mutant harbours a disabled cleavage site within the wild type factor X activation peptide. As expected when the mutant was tested at antigen levels equivalent to 216.4 U/ml factor X, the clotting activity reached only 0.5 mU/ml.

Recombinant wild type factor X derived from pFX532 as well as factor X variants derived from pFX535, pFX915 and pFX1066 were purified. Antigen as determined by ELISA using antibodies specific for factor X antigen concentrations ranged from 1.1 up to 4.3 U/ml. To exclude the disturbance of the measurement of factor X by factor Xa, factor Xa was determined by a chromogenic assay. All purified factor X variants contained only factor Xa levels of 0.023-0.103 mU/ml (Table 2), not significantly interfering with the factor X determination.

In order to compare the expressed factor X variants among each other, factor X clotting activities were determined and adjusted to about 1.5 U/ml. All the variants tested were functional active, resulting in clotting activities between 1.10 and 1.72 U/ml (Table 2).

Functionality of recombinant factor X variants in FVIII- and FIX deficient plasmas was tested in activated partial prothrombin time (aPPT) measuring the activity of the intrinsic coagulation cascade. 100 μl of FVIII- or FIX-depleted plasma was mixed with 100 μl of factor X variant cell culture supernatant or purified protein. After incubation for 6 minutes at 37° C. 100 μl of Pathromphtin (Dade Behring) containing $SiO_2$, phospholipids and 40 mM NaCl, as well as 100 μl of 25 mM $CaCl_2$ was added to start the coagulation reaction. Clotting time in seconds was determined by using a Schnittger & Gross coagulation timer. Activity was expressed as respective clotting FX equivalents as compared to standard human plasma.

The recombinant wild type factor X reached clotting activities of only 6.6 mU/ml in factor VIII depleted plasma and of only 5.8 mU/ml in FIX depleted plasma, as expected. In contrast, the factor X variants of the invention reached very high clotting activities ranging from 12952.0 to 26428.0 mU/ml in factor VIII depleted plasma and from 6327.0 mlU/ml to 15515.0 mlU/ml in FIX depleted plasma. (Table 2).

Factor X variant derived from pFX535 corresponds to factor X variants described in WO 01/10896 having the new factor IX activation sequence inserted within the region of the wild-type FX activation peptide N-terminal to Ile235, but with no deletion in the length of the activation peptide. Surprisingly the factor X variants of the invention in which the factor X wild-type activation peptide has been deleted and replaced with a novel protease cleavage site, encoded by pFX915 and pFX1066 developed very strong clotting activities of 6327.0 and 15515.0 mU/ml respectively in FIX depleted plasma or 12952.0 and 26428.0 mU/ml respectively in FVIII depleted plasma (Table 2).

Determination of functional activity was further performed using FVIII-inhibitor containing plasma from a haemophilia A patient. The patient plasma contained about 300 Bethesda Units of FVIII inhibitors per ml. Clotting was determined in aPPT and samples adjusted to factor X clotting as described above.

While the sample buffer control used for dilution of standards and test samples reached coagulation times of 156.5 seconds, recombinant wild type factor X reached coagulation times of 111.4 seconds. Confirming the surprising results in the FVIII or FIX clotting assay based on plasma depleted from FVIII or FIX, factor X variants of the invention encoded by pFX915 and pFX1066 led in a FEIBA assay based on a plasma containing FVIII inhibitory antibodies to clotting times of 21.4 and 21.1 seconds, respectively, being significantly shorter than the clotting times obtained when the factor X variant encoded by pFX535 was used (Table 2).

Altogether, it was shown that the factor X variants were functionally active as haemostatic bypassing agents, and that these factor X variants show clotting activity in haemophilia A patient plasma containing inhibitors against factor VIII. To our surprise, factor X variants encoded by pFX915 and pFX1066 showed much stronger clotting activities in factor VIII- and factor IX-depleted plasma, as compared to factor X variant encoded by pFX535 when adjusted to same factor X clotting equivalents.

TABLE 2

Determination of antigen and clotting activities of pFX532, pFX535, pFX915, and pFX1066

| Proteins expressed | FX equivalence | | FXa Activity (chromogenic assay) mIU/ml | Bypassing activities | | |
|---|---|---|---|---|---|---|
| | FX Antigen (ELISA) IU/ml | FX Activity (PT) IU/ml | | Activity (aPPT) in FVIII depleted plasma mIU/ml | Activity (aPPT) in FIX depleted plasma mIU/ml | FEIBA Activity (in FVIII inhibitor containing plasma) Clotting time (sec.) |
| pFX532 (wild type) | 4.3 | 1.72 | 0.028 | 6.6 | 5.8 | 111.4 |
| pFX535 (comparison) | 3.5 | 1.62 | 0.023 | 423.7 | 272.3 | 51.1 |
| pFX915 (example) | 1.1 | 1.28 | 0.103 | 12952.0 | 6327.0 | 21.4 |
| pFX1066 (example) | 1.4 | 1.10 | 0.028 | 26428.0 | 15515.0 | 21.1 |

Example 5

Purification of Recombinant Factor X Variants by Monoclonal Antibody Affinity Chromatography Recombinant factor X variants were purified according to the following protocol. Monoclonal antibodies FX-13 (ZLB Behring), specific for factor X, were coupled to CNBr-activated Sepharose. The resulting affinity resin was pored into a Pharmacia XK 16 chromatography column to form an affinity matrix of 1.6 cm in diameter and 1.8 cm in height, resulting in 3.6 ml of gel. The affinity matrix was stored in 2.5M NaCl, 10 mM di-sodium-hydrogen-phosphate. Before use, the gel was equilibrated with 10 gel-volumes of 20 mM tri-sodium citrate, 0.15M NaCl at pH 7.0-HCl.

Cell culture supernatant containing more than 100 mIU/ml factor X-antigen was dialysed using a VISKING tubing type 32/36, in 2-4 l of equilibration buffer at 4-8° C. over night.

Affinity-gel was loaded with 70 ml dialyzed supernatant at flow rates of 1 ml/min. Gel was washed with 10 volumes of equilibration buffer and subsequently eluted by 0.1M glycine, pH 2.5-HCl. The eluted material was neutralized by NaOH and stabilized by 1.0M NaCl and 0.1 mg/ml sodium caprylate.

Samples from cell culture supernatant of the factor X variant, from the flow through fraction and from the eluted material were analysed by SDS-PAGE and subsequent silver staining. A 58 kDa protein band was purified by the method described above. The 58 kDa band was identified as the factor X variant by Western blotting probed by anti-factor X antibodies.

The invention claimed is:

1. A biologically active factor X variant, comprising a full-length factor X polypeptide sequence with a modified factor X activation peptide, wherein the modified activation peptide has a formula of —$R^1$—P—$R^2$—wherein P is a polypeptide sequence cleavable by a serine protease, $R^1$ is a chemical bond or one or more amino acids, and $R^2$ is a chemical bond or one or more amino acids, wherein the modified activation peptide of —$R^1$—P—$R^2$—consists of a polypeptide sequence having a total length of 3-9 amino acids and the P is not present within an activation peptide of a wild type factor X (amino acid positions Ser183 through Arg234 of SEQ ID NO:2) and replaces the activation peptide of the wild type Factor X, wherein cleavage at the P by the serine protease activates the factor X variant, wherein the serine protease is factor IIa, factor IXa, factor Xa, factor XIa, factor XIIa, activated protein C, elastase, or kallikrein, and is not furin4 and wherein the factor X variant has factor X coagulant activity.

2. The factor X variant according to claim 1, wherein the factor X variant has an enhanced haemostatic bypassing activity compared to that of a factor X variant wherein —$R^1$—P—$R^2$—consists of the amino acid sequence of SEQ ID NO:3.

3. The factor X variant according to claim 1, wherein the factor X variant has an enhanced haemostatic bypassing activity compared to that of a factor X variant wherein —$R^1$—P—$R^2$—consists of the amino acid sequence Glu226-Gln227-Ser228-Phe229-Asn230-Asp231-Phe232-Thr233-Arg234 (SEQ ID NO:10).

4. A pharmaceutical composition comprising the factor X variant according to claim 1 and a pharmaceutically acceptable carrier or excipient.

* * * * *

```
                        SEQUENCE LISTING

<160> NUMBER OF SEQ ID NOS: 30

<210> SEQ ID NO 1
<211> LENGTH: 1467
<212> TYPE: DNA
<213> ORGANISM: Human

<400> SEQUENCE: 1 atgggcgcc  cactgcacct  cgtcctgctc  agtgcctccc  tggctggcct  cctgctgctc      60
ggggaaagtc  tgttcatccg  cagggagcag  gccaacaaca  tcctggcgag  ggtcacgagg     120
gccaattcct  ttcttgaaga  gatgaagaaa  ggacacctcg  aaagagagtg  catggaagag     180
acctgctcat  acgaagaggc  ccgcgaggtc  tttgaggaca  gcgacaagac  gaatgaattc     240
tggaataaat  acaaagatgg  cgaccagtgt  gagaccagtc  cttgccagaa  ccagggcaaa     300
tgtaaagacg  gcctcgggga  atacacctgc  acctgtttag  aaggattcga  aggcaaaaac     360
tgtgaattat  tcacacggaa  gctctgcagc  ctggacaacg  gggactgtga  ccagttctgc     420
cacgaggaac  agaactctgt  ggtgtgctcc  tgcgcccgcg  ggtacaccct  ggctgacaac     480
ggcaaggcct  gcattccac   agggccctac  ccctgtggga  acagaccct   ggaacgcagg     540 aagaggtcag  tgcccaggc   caccagcagc  agcggggagg  ccctgacag   catcacatgg     600 aagccatatg  atgcagccga  cctggacccc  accgagaacc  ccttcgacct  gcttgacttc     660
aaccagacgc  agcctgagag  gggcgacaac  aacctcacca  ggatcgtggg  aggccaggaa     720
```

```
tgcaaggacg gggagtgtcc ctggcaggcc ctgctcatca atgaggaaaa cgagggtttc    780
tgtggtggaa ccattctgag cgagttctac atcctaacgg cagcccactg tctctaccaa    840
gccaagagat tcaaggtgag ggtaggggac cggaacacgg agcaggagga gggcggtgag    900
gcggtgcacg aggtggaggt ggtcatcaag cacaaccggt tcacaaagga gacctatgac    960
ttcgacatcg ccgtgctccg gctcaagacc cccatcacct tccgcatgaa cgtggcgcct   1020
gcctgcctcc ccgagcgtga ctgggccgag tccacgctga tgacgcagaa gacggggatt   1080
gtgagcggct tcgggcgcac ccacgagaag ggccggcagt ccaccaggct caagatgctg   1140
gaggtgccct acgtgaccg caacagctgc aagctgtcca gcagcttcat catcacccag   1200
aacatgttct gtgccggcta cgacaccaag caggaggatg cctgccaggg ggacagcggg   1260
ggcccgcacg tcacccgctt caaggacacc tacttcgtga caggcatcgt cagctgggga   1320
gagggctgtg cccgtaaggg gaagtacggg atctacacca aggtcaccgc cttcctcaag   1380
tggatcgaca ggtccatgaa aaccaggggc ttgcccaagg ccaagagcca tgccccggag   1440
gtcataacgt cctctccatt aaagtga                                       1467
```

<210> SEQ ID NO 2
<211> LENGTH: 488
<212> TYPE: PRT
<213> ORGANISM: Human

<400> SEQUENCE: 2

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240
```

```
Cys Lys Asp Gly Glu Cys Pro Trp Gln Ala Leu Leu Ile Asn Glu Glu
            245                 250                 255

Asn Glu Gly Phe Cys Gly Gly Thr Ile Leu Ser Glu Phe Tyr Ile Leu
        260                 265                 270

Thr Ala Ala His Cys Leu Tyr Gln Ala Lys Arg Phe Lys Val Arg Val
    275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 3
<211> LENGTH: 9
<212> TYPE: PRT
<213> ORGANISM: Human

<400> SEQUENCE: 3

Thr Gln Ser Phe Asn Asp Phe Thr Arg
1               5

<210> SEQ ID NO 4
<211> LENGTH: 52
<212> TYPE: PRT
<213> ORGANISM: Human

<400> SEQUENCE: 4

Ser Val Ala Gln Ala Thr Ser Ser Gly Glu Ala Pro Asp Ser Ile
1               5                   10                  15

Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
        35                  40                  45

Asn Leu Thr Arg
    50
```

```
<210> SEQ ID NO 5
<211> LENGTH: 12
<212> TYPE: PRT
<213> ORGANISM: Human

<400> SEQUENCE: 5

Leu Glu Lys Arg Asn Ala Ser Lys Pro Gln Gly Arg
1               5                   10

<210> SEQ ID NO 6
<211> LENGTH: 35
<212> TYPE: PRT
<213> ORGANISM: Human

<400> SEQUENCE: 6

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 7
<211> LENGTH: 16
<212> TYPE: PRT
<213> ORGANISM: Human

<400> SEQUENCE: 7

Gly Ser Glu Ala Ala Ala Ser Thr Ala Val Val Ile Ala Gly Arg Ser
1               5                   10                  15

<210> SEQ ID NO 8
<211> LENGTH: 445
<212> TYPE: PRT
<213> ORGANISM: Human
<220> FEATURE:
<221> NAME/KEY: PROPEP
<222> LOCATION: (1)..(40)
<220> FEATURE:
<221> NAME/KEY: MUTAGEN
<222> LOCATION: (39)..(39)
<223> OTHER INFORMATION: T39R

<400> SEQUENCE: 8

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
```

130                 135                 140
Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Thr Gln Ser Phe Asn Asp Phe Thr Arg Ile
                180                 185                 190

Val Gly Gly Gln Glu Cys Lys Asp Gly Glu Cys Pro Trp Gln Ala Leu
            195                 200                 205

Leu Ile Asn Glu Glu Asn Glu Gly Phe Cys Gly Gly Thr Ile Leu Ser
            210                 215                 220

Glu Phe Tyr Ile Leu Thr Ala Ala His Cys Leu Tyr Gln Ala Lys Arg
225                 230                 235                 240

Phe Lys Val Arg Val Gly Asp Arg Asn Thr Glu Gln Glu Glu Gly Gly
                245                 250                 255

Glu Ala Val His Glu Val Glu Val Val Ile Lys His Asn Arg Phe Thr
                260                 265                 270

Lys Glu Thr Tyr Asp Phe Asp Ile Ala Val Leu Arg Leu Lys Thr Pro
            275                 280                 285

Ile Thr Phe Arg Met Asn Val Ala Pro Ala Cys Leu Pro Glu Arg Asp
290                 295                 300

Trp Ala Glu Ser Thr Leu Met Thr Gln Lys Thr Gly Ile Val Ser Gly
305                 310                 315                 320

Phe Gly Arg Thr His Glu Lys Gly Arg Gln Ser Thr Arg Leu Lys Met
                325                 330                 335

Leu Glu Val Pro Tyr Val Asp Arg Asn Ser Cys Lys Leu Ser Ser Ser
                340                 345                 350

Phe Ile Ile Thr Gln Asn Met Phe Cys Ala Gly Tyr Asp Thr Lys Gln
            355                 360                 365

Glu Asp Ala Cys Gln Gly Asp Ser Gly Gly Pro His Val Thr Arg Phe
370                 375                 380

Lys Asp Thr Tyr Phe Val Thr Gly Ile Val Ser Trp Gly Glu Gly Cys
385                 390                 395                 400

Ala Arg Lys Gly Lys Tyr Gly Ile Tyr Thr Lys Val Thr Ala Phe Leu
                405                 410                 415

Lys Trp Ile Asp Arg Ser Met Lys Thr Arg Gly Leu Pro Lys Ala Lys
            420                 425                 430

Ser His Ala Pro Glu Val Ile Thr Ser Ser Pro Leu Lys
            435                 440                 445

<210> SEQ ID NO 9
<211> LENGTH: 445
<212> TYPE: PRT
<213> ORGANISM: Human
<220> FEATURE:
<221> NAME/KEY: PROPEP
<222> LOCATION: (1)..(40)
<220> FEATURE:
<221> NAME/KEY: MUTAGEN
<222> LOCATION: (39)..(39)
<223> OTHER INFORMATION: T39R

<400> SEQUENCE: 9

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

```
Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
 50                  55                  60

Glu Glu Ala Arg Glu Val Phe Glu Asp Ser Asp Lys Thr Asn Glu Phe
 65                  70                  75                  80

Trp Asn Lys Tyr Lys Asp Gly Asp Gln Cys Glu Thr Ser Pro Cys Gln
                 85                  90                  95

Asn Gln Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Thr Gln Ser Phe Asn Asp Phe Thr Arg Val
            180                 185                 190

Val Gly Gly Gln Glu Cys Lys Asp Gly Glu Cys Pro Trp Gln Ala Leu
        195                 200                 205

Leu Ile Asn Glu Glu Asn Glu Gly Phe Cys Gly Gly Thr Ile Leu Ser
    210                 215                 220

Glu Phe Tyr Ile Leu Thr Ala Ala His Cys Leu Tyr Gln Ala Lys Arg
225                 230                 235                 240

Phe Lys Val Arg Val Gly Asp Arg Asn Thr Glu Gln Glu Glu Gly Gly
                245                 250                 255

Glu Ala Val His Glu Val Glu Val Val Ile Lys His Asn Arg Phe Thr
            260                 265                 270

Lys Glu Thr Tyr Asp Phe Asp Ile Ala Val Leu Arg Leu Lys Thr Pro
        275                 280                 285

Ile Thr Phe Arg Met Asn Val Ala Pro Ala Cys Leu Pro Glu Arg Asp
    290                 295                 300

Trp Ala Glu Ser Thr Leu Met Thr Gln Lys Thr Gly Ile Val Ser Gly
305                 310                 315                 320

Phe Gly Arg Thr His Glu Lys Gly Arg Gln Ser Thr Arg Leu Lys Met
                325                 330                 335

Leu Glu Val Pro Tyr Val Asp Arg Asn Ser Cys Lys Leu Ser Ser Ser
            340                 345                 350

Phe Ile Ile Thr Gln Asn Met Phe Cys Ala Gly Tyr Asp Thr Lys Gln
        355                 360                 365

Glu Asp Ala Cys Gln Gly Asp Ser Gly Gly Pro His Val Thr Arg Phe
    370                 375                 380

Lys Asp Thr Tyr Phe Val Thr Gly Ile Val Ser Trp Gly Glu Gly Cys
385                 390                 395                 400

Ala Arg Lys Gly Lys Tyr Gly Ile Tyr Thr Lys Val Thr Ala Phe Leu
                405                 410                 415

Lys Trp Ile Asp Arg Ser Met Lys Thr Arg Gly Leu Pro Lys Ala Lys
            420                 425                 430

Ser His Ala Pro Glu Val Ile Thr Ser Ser Pro Leu Lys
    435                 440                 445
```

-continued

```
<210> SEQ ID NO 10
<211> LENGTH: 9
<212> TYPE: PRT
<213> ORGANISM: Human

<400> SEQUENCE: 10

Glu Gln Ser Phe Asn Asp Phe Thr Arg
1               5

<210> SEQ ID NO 11
<211> LENGTH: 20
<212> TYPE: DNA
<213> ORGANISM: Artificial
<220> FEATURE:
<223> OTHER INFORMATION: Mutagenesis oligonucleotide We1292

<400> SEQUENCE: 11
cagggacaca gtactcggcc                                              20

<210> SEQ ID NO 12
<211> LENGTH: 22
<212> TYPE: DNA
<213> ORGANISM: Artificial
<220> FEATURE:
<223> OTHER INFORMATION: Mutagenesis oligonucleotide We1293

<400> SEQUENCE: 12
gagtgggatc tcactttaat gg                                           22

<210> SEQ ID NO 13
<211> LENGTH: 28
<212> TYPE: DNA
<213> ORGANISM: Artificial
<220> FEATURE:
<223> OTHER INFORMATION: Mutagenesis oligonucleotide We1354

<400> SEQUENCE: 13
gcggctagca tggggcgccc actgcacc                                     28

<210> SEQ ID NO 14
<211> LENGTH: 36
<212> TYPE: DNA
<213> ORGANISM: Artificial
<220> FEATURE:
<223> OTHER INFORMATION: Mutagenesis oligonucleotide We1355

<400> SEQUENCE: 14
gcggcggccg ctcactttaa tggagaggac gttatg                            36

<210> SEQ ID NO 15
<211> LENGTH: 27
<212> TYPE: DNA
<213> ORGANISM: Artificial
<220> FEATURE:
<223> OTHER INFORMATION: Mutagenesis oligonucleotide We1482

<400> SEQUENCE: 15
cctggcgagg gtcaggaggg ccaattc                                      27

<210> SEQ ID NO 16
<211> LENGTH: 27
<212> TYPE: DNA
<213> ORGANISM: Artificial
<220> FEATURE:
<223> OTHER INFORMATION: Mutagenesis oligonucleotide We1483
```

<400> SEQUENCE: 16
gaattggccc tcctgaccct cgccagg                                          27

<210> SEQ ID NO 17
<211> LENGTH: 50
<212> TYPE: DNA
<213> ORGANISM: Artificial
<220> FEATURE:
<223> OTHER INFORMATION: Mutagenesis oligonucleotide We1444

<400> SEQUENCE: 17
cagacgcagc ctacccaatc atttaatgac ttcactcgga tcgtgggagg                  50

<210> SEQ ID NO 18
<211> LENGTH: 50
<212> TYPE: DNA
<213> ORGANISM: Artificial
<220> FEATURE:
<223> OTHER INFORMATION: Mutagenesis oligonucleotide We1445

<400> SEQUENCE: 18
cctcccacga tccgagtgaa gtcattaaat gattgggtag gctgcgtctg                  50

<210> SEQ ID NO 19
<211> LENGTH: 28
<212> TYPE: DNA
<213> ORGANISM: Artificial
<220> FEATURE:
<223> OTHER INFORMATION: Mutagenesis oligonucleotide We1567

<400> SEQUENCE: 19
ggcgacaaca acgacgacag gatcgtgg                                         28

<210> SEQ ID NO 20
<211> LENGTH: 28
<212> TYPE: DNA
<213> ORGANISM: Artificial
<220> FEATURE:
<223> OTHER INFORMATION: Mutagenesis oligonucleotide We1568

<400> SEQUENCE: 20
ccacgatcct gtcgtcgttg ttgtcgcc                                         28

<210> SEQ ID NO 21
<211> LENGTH: 32
<212> TYPE: DNA
<213> ORGANISM: Artificial
<220> FEATURE:
<223> OTHER INFORMATION: Mutagenesis oligonucleotide We1976

<400> SEQUENCE: 21
gcaggaagag gacccaatca tttaatgact tc                                    32

<210> SEQ ID NO 22
<211> LENGTH: 32
<212> TYPE: DNA
<213> ORGANISM: Artificial
<220> FEATURE:
<223> OTHER INFORMATION: Mutagenesis oligonucleotide We1977

<400> SEQUENCE: 22
gaagtcatta aatgattggg tcctcttcct gc                                    32

<210> SEQ ID NO 23
<211> LENGTH: 25

-continued

<210> SEQ ID NO 23
<211> LENGTH: 25
<212> TYPE: DNA
<213> ORGANISM: Artificial
<220> FEATURE:
<223> OTHER INFORMATION: Mutagenesis oligonucleotide We2357

<400> SEQUENCE: 23
cgacttcacc cgcgtcgtgg gaggc        25

<210> SEQ ID NO 24
<211> LENGTH: 25
<212> TYPE: DNA
<213> ORGANISM: Artificial
<220> FEATURE:
<223> OTHER INFORMATION: Mutagenesis oligonucleotide We2358

<400> SEQUENCE: 24
gcctcccacg acgcgggtga agtcg        25

<210> SEQ ID NO 25
<211> LENGTH: 5
<212> TYPE: PRT
<213> ORGANISM: Artificial
<220> FEATURE:
<223> OTHER INFORMATION: Modified activation peptide in factor X variant

<400> SE

-continued

```
<400> SEQUENCE: 28

Pro Tyr Pro Cys Gly Lys Gln Thr Leu Glu Arg Arg Lys Arg Ser Val
1               5                   10                  15

Ala Gln Ala Thr Ser Ser Ser Gly Glu Ala Pro Asp Ser Ile Thr Trp
            20                  25                  30

Lys Pro Tyr Asp Ala Ala Asp Leu Asp Pro Thr Glu Asn Pro Phe Asp
        35                  40                  45

Leu Leu Asp Phe Asn Gln Thr Gln Pro Thr Gln Ser Phe Asn Asp Phe
    50                  55                  60

Thr Arg Ile Val Gly Gly Gln Glu Cys Lys Asp
65                  70                  75

<210> SEQ ID NO 29
<211> LENGTH: 32
<212> TYPE: PRT
<213> ORGANISM: Artificial
<220> FEATURE:
<223> OTHER INFORMATION: Modified activation peptide in factor X variant

<400> SEQUENCE: 29

Pro Tyr Pro Cys Gly Lys Gln Thr Leu Glu Arg Arg Lys Arg Thr Gln
1               5                   10                  15

Ser Phe Asn Asp Phe Thr Arg Ile Val Gly Gly Gln Glu Cys Lys Asp
            20                  25                  30

<210> SEQ ID NO 30
<211> LENGTH: 32
<212> TYPE: PRT
<213> ORGANISM: Artificial
<220> FEATURE:
<223> OTHER INFORMATION: Modified activation peptide in factor X variant

<400> SEQUENCE: 30

Pro Tyr Pro Cys Gly Lys Gln Thr Leu Glu Arg Arg Lys Arg Thr Gln
1               5                   10                  15

Ser Phe Asn Asp Phe Thr Arg Val Val Gly Gly Gln Glu Cys Lys Asp
            20                  25                  30
```